United States Patent [19]

Foster

[11] 4,222,949
[45] Sep. 16, 1980

[54] PROCESS FOR SEPARATING STIGMASTEROL-DERIVED PRODUCTS (II)

[75] Inventor: Charles H. Foster, Kingsport, Tenn.

[73] Assignee: Eastman Kodak Company, Rochester, N.Y.

[21] Appl. No.: 68,033

[22] Filed: Aug. 20, 1979

[51] Int. Cl.$^2$ .............................................. C07J 9/00
[52] U.S. Cl. .............................................. 260/397.25
[58] Field of Search .................................. 260/397.25

[56] References Cited

U.S. PATENT DOCUMENTS 3,803,184   4/1974   Njimi et al. ..................... 260/397.25

Primary Examiner—Elbert L. Roberts
Attorney, Agent, or Firm—Clyde L. Tootle; Daniel B. Reece, III

[57] ABSTRACT

This invention relates to the separation of crude mixtures of sterols, and more particularly it relates to the removal of stigmasterol derived products from crude mixtures of sterols. The present invention relates more specifically to a process for separating stigmasterol-derived products from phytosterol materials containing mixtures of stigmasterol, sitosterol and campesterol. These mixtures are reacted to form the corresponding $\Delta^4$-3-keto derivatives of phytosterols. The $\Delta^4$-3-keto derivatives of phytosterols are reacted by ozonolysis to form the 4-stigmasten-3-one-derived aldehyde material, 3-ketodinor-4-cholen-22-aldehyde, which can be isolated from the other $\Delta^4$-3-keto derivatives of phytosterol by either chromatography or by treatment with sodium bisulfite and extraction with a suitable organic solvent such as toluene.

5 Claims, No Drawings

PROCESS FOR SEPARATING STIGMASTEROL-DERIVED PRODUCTS (II)

This invention relates to the separation of crude mixtures of sterols, and more particularly it relates to the removal of stigmasterol derived products from crude mixtures of sterols. The present invention relates more specifically to an improved process for separating stigmasterol-derived products from phytosterol materials which contain mixtures of stigmasterol, sitosterol and campesterol. These phytosterol mixtures are reacted to form the corresponding $\Delta^4$-3-keto derivatives of phytosterols. The $\Delta^4$-3-keto derivatives of phytosterols are reacted by ozonolysis to form the 4-stigmasten-3-one-derived aldehyde material, 3-ketodinor-4-cholen-22-aldehyde, which can be isolated from the other $\Delta^4$-3-keto derivatives of phytosterol by either chromatography or by treatment with sodium bisulfite and extraction with a suitable organic solvent such as toluene.

The naturally occurring phytosterol components of vegetable oils are composed of mixtures of phytosterols which have similar chemical and physical properties which make separation of the phytosterols into individual components difficult. For example, oils such a soybean oil contain phytosterols which are mixtures of about 25 percent stigmasterol, about 75 percent sitosterol and campesterol. The stigmasterol is extremely difficult to separate from the sitosterol because the two compounds differ structurally by a single double bond in the aliphatic side chain. The separation of the stigmasterol from sitosterol and the other phytosterols such as campesterol is important since the stigmasterol can be used in the preparation of certain pharmaceuticals such as progesterone which also can be used to prepare other steroids, cortisone and the like.

Previously, the separation of stigmasterol from the other phytosterols in phytosterol mixtures has been carried out by the Winders and Hauth bromination method whereby a mixture of physterol acetates is brominated, crystallizing out the relatively insoluble stigmasterol acetate tetrabromide, and separating stigmasterol therefrom. However, this bromination procedure is not entirely satisfactory for large scale commercial processes for the separation of stigmasterol since it is a relatively expensive process, and the yields are reported to be low.

Other processes, such as extraction or leaching processes, have also been developed and used in commercial processes for separation of stigmasterol. These extraction or leaching processes often involve countercurrent extraction or leaching employing large amounts of different solvents and require extensive processing steps and expensive equipment and substantial amounts of labor and energy to isolate stigmasterol. It would therefore be a significant advance in the state of the art to provide a relatively simple, less expensive and less energy and labor consuming process useful commercially to separate stigmasterol from other phytosterols.

In accordance with the present invention, mixtures of phytosterol compositions containing stigmasterol are reacted to form the $\Delta^4$-3-keto derivatives of phytosterols. Any conventional process known in the art can be used to react the crude mixture of sterols to obtain the $\Delta^4$-3-keto derivatives of phytosterol used in the ozonization and separation. Such processes known in the art for forming the $\Delta^4$-3-keto derivatives include the catalytic oxidation of $\Delta^5$-sterols to ketones with a simultaneous shift of the $\Delta^5$ double bond to the $\Delta^4$ position in conjugation with the carbonyl group. This transformation is usually carried out via an Oppenauer oxidation such as *Recl. Trav. Chim. Pays-Bas.*, 56, 137 (1937). Raney nickel has also been used for this reaction, either in presence of excess catalyst, as for example, Chakravarti, Chakravarti, and Metra, *Nature*, 193, 1071 (1962) or in the presence of a hydrogen acceptor, as for example, E. C. Kleiderer, and E. C. Kornfeld, *J. Org. Chem.*, 13, 455 (1948) and Kleiderer, Rice, Conquest and Williams, U.S. Dept. of Commerce, Office of the Publication board, Report PB 981, 1945.

These mixed $\Delta^4$-3-keto derivatives of phytosterol are then treated with ozone or a mixture of ozone and oxygen at a temperature of about $-80°$ C. to about $0°$ C. in a suitable solvent such as a 3:1 to 1:3 methylene dichloride/methyl alcohol solvent. The ozonide is reduced with trimethyl phosphite and the mixture can be washed with aqueous sodium sulfite, then washed with water, and the product subsequently dried over sodium sulfate. The solvent is then evaporated to provide a yellow oil containing a mixture of 3-ketodinor-4-cholen-22-aldehyde and the $\Delta^4$-3-keto derivatives of sitosterol and campesterol. The 3-ketodinor-4-cholen-22-aldehyde can be separated from this mixture by chromatography or by preparing the bisulfite adduct. The 3-ketodinor-4-cholen-22-aldehyde can be used as a starting material to prepare other steroids such as progesterone, for example.

The ozonide can be reduced by other reducing means in place of the trimethyl phosphite. For example, alternate reducing agents such as the combination of zinc and acetic acid, sodium bisulfite, dimethyl sulfide, formaldehyde and the like reducing agents can also be used.

This invention can be further illustrated by the following examples, although it will be understood that these examples are included merely for purposes of illustration and are not intended to limit the scope of the invention unless otherwise specifically indicated.

EXAMPLE

Preparation of $\Delta^4$-3-Keto Soy Steroids

To 150 g. of mixed soy sterols in a 2 l. flask was added 1030 g. cyclohexanone and 100 ml of toluene. The solution was heated to reflux to remove a small amount of water and aluminum isopropoxide (prepared from 6.75 g. aluminum and 17.5 ml isopropyl alcohol by the procedure of A. L. Wilds, *Org. Reactions*, 2, 178 (1944) was added, heated to reflux for 15 minutes and then steam distilled to remove excess cyclohexanone. The residue was diluted with water and acidified with conc. hydrochloric acid and extracted with hexane. The hexane solution was washed three times with water and dried with anhydrous sodium sulfate. The hexane solution was put through a column packed with commercial Doucil (2.4 in $\times$23 in.). Some of the $\Delta^4$-3-keto steriods were eluted with hexane in the first fraction with cyclohexylidine cyclohexanone. Elution with 3% acetone in hexane gave 73.3 g. of $\Delta^4$-3-keto soy steroids.

The mixture of $\Delta^4$-3-keto soy steroids is then treated with ozone to prepare 3-ketodinor-4-cholen-22-aldehyde. The ozonization is carried out by a stream of $O_3/O_2$ being passed through a solution of $\Delta^4$-3-ketosoy steriods in 280 ml of methylene chloride containing 3.5 ml. of pyridine at $-65°$ to $-75°$ C. until all of the 4, 22-stigmastadiene-3-one has been reacted as measured by VPC analysis. The mixture was flushed with $N_2$ to remove excess ozone and then treated with 12.5 g. zinc dust and 25 ml of glacial acetic acid. After stirring 2 hrs. at ambient temperature the excess zinc dust was filtered on celite and rinsed with hexane. The filtrate was washed with water and dried with anhydrous $Na_2SO_4$.

A. Process for separating stigmasterol-derived products by chromotography.

To a column packed with commercial Doucil (2.4 in. ×23 in.) was added 28 g of the oil recovered above in 100 ml of hexane. Elution of the unreacted $\Delta^4$-3-keto steroids with heptane (1250 ml) and with 3% acetone in hexane followed by elution of 3-keto-dinor-4-cholen aldehyde with 30% acetone in hexane gave 9.38 g. of oil shown by VPC to be essentially pure 3-keto-dinor-4-cholen aldehyde.

B. Process for separating stigmasterol-derived products by the bisulfite adduct. The ozonolysis product ($\Delta^4$-3-keto steroids) (29.0 g) was mixed with ethyl alcohol (200 ml). A saturated aqueous sodium bisulfate solution (250 ml) was added and the mixture was refluxed 1 hr. The mixture was cooled to 10° C. and a white solid was isolated by filtration. The solid was washed with toluene. Evaporation of toluene gave 19.0 g of oil, shown by VPC analysis to be unreacted $\Delta^4$-3-keto steroids. The original ethyl alcohol/water/sodium bisulfite filtrate can be further extracted with toluene. Evaporation of the toluene layer gave 3-keto-dinor-4-cholen-22-aldehyde as a viscous oil (7.5 g).

Alternatively, the ozonolysis product ($\Delta^4$-3-keto steroids) (17.0 g), dissolved in EtOH (150 ml) was treated with a solution prepared from 12 ml of EtOH and 48 ml $NaHSO_3$ saturated aqueous solution. The mixture was heated on a steam bath 1–5 hrs., then allowed to cool to room temperature. The precipitate obtained was filtered off and treated with 100 ml of 5% NaOH. Filtration of this mixture gave 3-keto-dinor-4-cholen-22-aldehyde in 69% yield.

The process of the present invention provides an improved method for separating stigmasterol derivatives from phytosterol mixtures containing stigmasterol, sitosterol and campesterol. Further, the stigmasterol derivatives can be used to provide starting materials for preparation of valuable steroids.

The invention has been described in detail with particular reference to preferred embodiments thereof, but it will be understood that variations and modifications can be effected within the spirit and scope of the invention.

I claim:

1. A process which comprises treating a crude mixture of sterols containing stigmasterol to form the $\Delta^4$-3-keto derivatives of said sterols, ozonizing the $\Delta^4$-3-keto sterol derivatives, reducing the phytosterol ozonide and thereafter recovering 3-keto-dinor-4-cholen-22-aldehyde from the reaction mixture.

2. A process according to claim 1 wherein said 3-keto-dinor-4-cholen-22-aldehyde is separated from said reaction mixture by chromatography.

3. A process according to claim 1 wherein said 3-keto-dinor-4-cholen-22-aldehyde is separated from said reaction mixture by treating said reaction mixture with an aqueous solution of sodium bisulfite and alkanol, filtering the bisulfite treated reaction mixture and thereafter extracting the aqueous/alkanol filtrate with a suitable organic solvent and removal of the solvent to obtain 3-keto-dinor-4-cholen-22-aldehyde.

4. A process according to claim 1 wherein said ozonizing is carried out by treating with a mixture of ozone and oxygen and at a temperature of about −80° C. to about 0° C.

5. A process according to claim 4 wherein said reducing is carried out with trimethyl phosphite.

* * * * *